(12) United States Patent
Richardson et al.

(10) Patent No.: US 6,402,706 B2
(45) Date of Patent: Jun. 11, 2002

(54) GUIDE WIRE WITH MULTIPLE POLYMER JACKETS OVER DISTAL AND INTERMEDIATE CORE SECTIONS

(75) Inventors: Mark Richardson, Escondido; Emmanuel C. Biagtan, Temecula; Wayne E. Cornish, Oceanside, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/223,223

(22) Filed: Dec. 30, 1998

(51) Int. Cl.[7] ................................................. A61B 5/00
(52) U.S. Cl. ..................................................... 600/585
(58) Field of Search ................................. 600/585, 657, 600/658; 604/280–282

(56) References Cited

U.S. PATENT DOCUMENTS

| | | | |
|---|---|---|---|
| 5,452,726 A | * | 9/1995 | Burmeister et al. ......... 600/585 |
| 5,498,250 A | | 3/1996 | Prather ........................ 604/280 |
| 5,772,609 A | * | 6/1998 | Nguyen et al. ............. 600/585 |
| 5,830,181 A | * | 11/1998 | Thornton .................... 604/102 |
| 6,019,736 A | * | 2/2000 | Avellanet et al. ........... 600/585 |

* cited by examiner

*Primary Examiner*—Max Hindenburg
(74) *Attorney, Agent, or Firm*—Fulwider Patton Lee & Utecht, LLP

(57) ABSTRACT

The invention is directed to a guide wire having at least two different polymeric jackets that impart different handling characteristics to the portions of the guide wire they surround. Preferably, the guide wire may have jackets of different grades of polymer, such as polyurethane 55 D and 90 A. Alternatively, the guide wire may have jackets of different types of polymers such as polyurethane and polytetrafluoroethylene, or may have a single polymeric jacket with continuously varying properties along its length. The invention also comprises methods of making such guide wires.

10 Claims, 4 Drawing Sheets

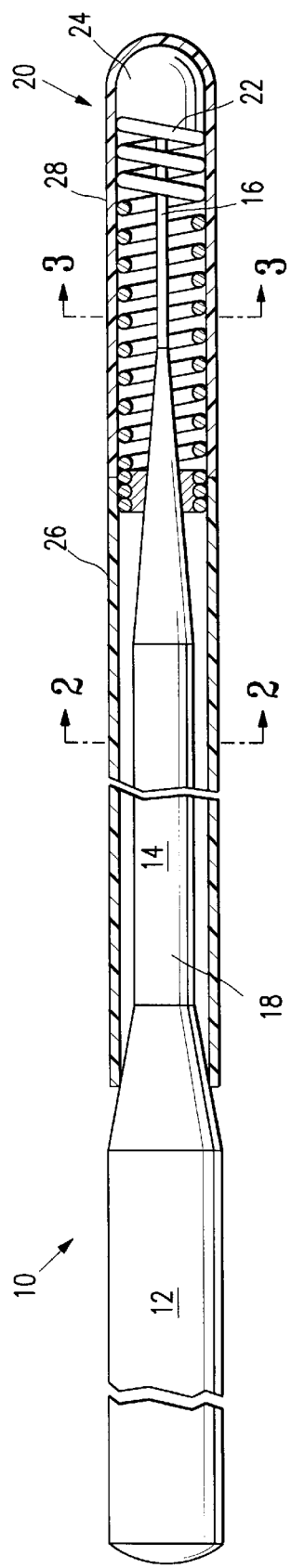
FIG. 1
FIG. 3
FIG. 2

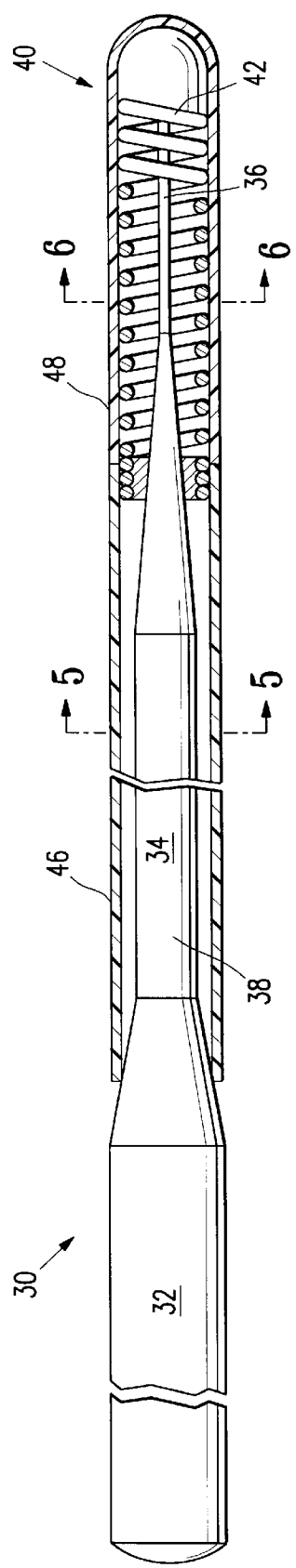
FIG. 4
FIG. 6
FIG. 5

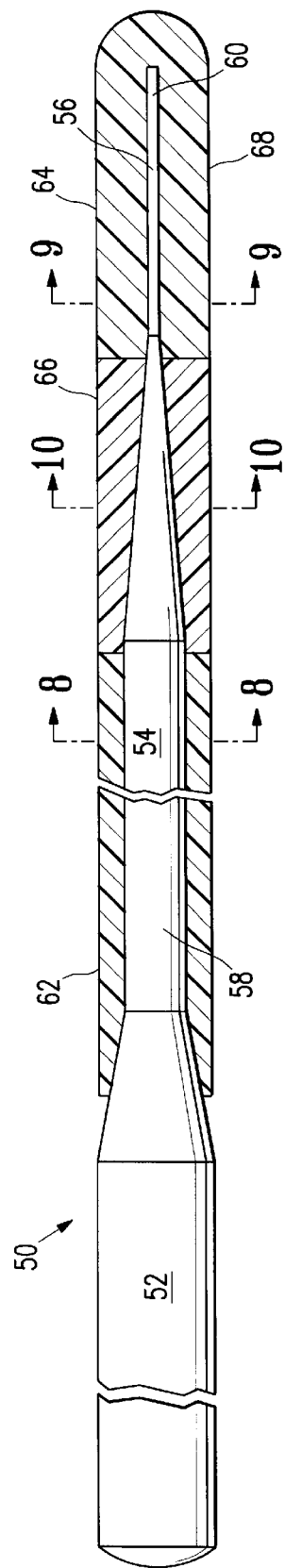
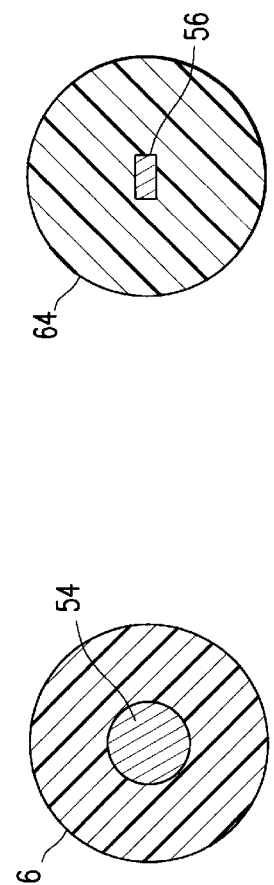
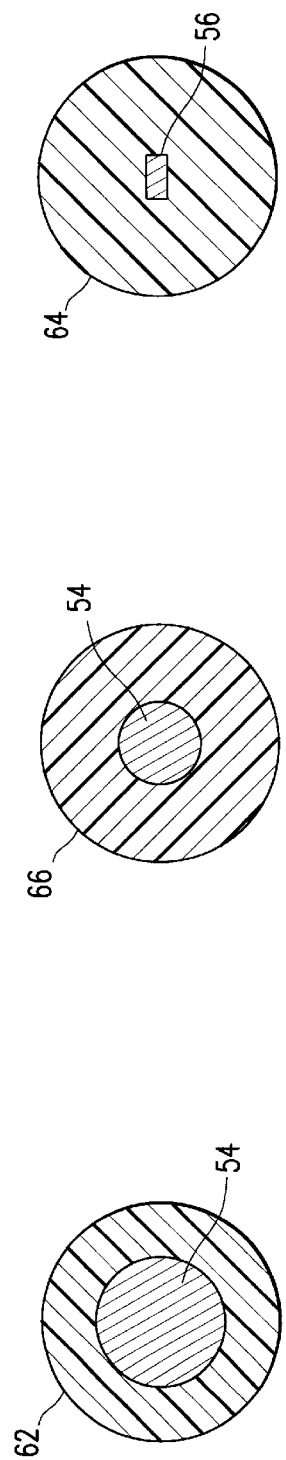

GUIDE WIRE WITH MULTIPLE POLYMER JACKETS OVER DISTAL AND INTERMEDIATE CORE SECTIONS

BACKGROUND OF THE INVENTION

This invention relates to the field of guide wires for advancing intraluminal devices such as stent delivery catheters, balloon dilatation catheters, atherectomy catheters and the like within body lumens.

In a typical percutaneous procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of the desired coronary artery. There are two basic techniques for advancing a guide wire into the desired location within the patient's coronary anatomy, the first is a pre-load technique which is used primarily for over-the-wire (OTW) devices and the bare wire technique which is used primarily for rail type systems.

With the pre-load technique, a guide wire is positioned within an inner lumen of an OTW device such as a dilatation catheter or stent delivery catheter with the distal tip of the guide wire just proximal to the distal tip of the catheter and then both are advanced through the guiding catheter to the distal end thereof. The guide wire is first advanced out of the distal end of the guiding catheter into the patient's coronary vasculature until the distal end of the guide wire crosses the arterial location where the interventional procedure is to be performed, e.g. a lesion to be dilated or a dilated region where a stent is to be deployed. The catheter, which is slidably mounted onto the guide wire, is advanced out of the guiding catheter into the patient's coronary anatomy by sliding over the previously introduced guide wire until the operative portion of the intravascular device, e.g. the balloon of a dilatation or a stent delivery catheter, is properly positioned across the arterial location. Once the catheter is in position with the operative means located within the desired arterial location, the interventional procedure is performed.

With the bare wire technique, the guide wire is first advanced by itself through the guiding catheter until the distal tip of the guide wire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guide wire which extends out of the proximal end of the guiding catheter which is outside of the patient. The catheter is advanced over the guide wire, while the position of the guide wire is fixed, until the operative means on the rail type catheter is disposed within the arterial location where the procedure is to be performed. After the procedure the intravascular device may be withdrawn from the patient over the guide wire or the guide wire repositioned within the coronary anatomy for an additional procedure.

Further details of guide wires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

Conventional guide wires for angioplasty, stent delivery, atherectomy and other vascular procedures usually comprise an elongate core member with one or more tapered sections near the distal end thereof and a flexible body member such as a helical coil or a tubular body of polymeric material disposed about the distal portion of the core member. A shapeable member, which may be the distal extremity of the core member or a separate shapeable ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guide wire while it is being advanced through a patient's vascular system.

A problem confronting designers of successful guide wires is the desirability to provide different physical characteristics for different parts of the guide wire. For example, many guide wires have a highly flexible leading tip designed not to damage or perforate the vessel. Further, the portion behind the distal tip is increasingly stiff to better support a balloon catheter or similar device. The more proximal portion of the guide wire must also have sufficient torsional rigidity to allow the tip to be steered through the coronary vasculature.

One solution that has been employed is to provide a guide wire having a core member with tapered diameters as discussed above. However, it can be difficult to obtain the desired handling characteristics on the basis of core wire dimensions alone. Other solutions have involved the use of different materials for different portions of the guide wire. These attempts raise new problems in obtaining appropriately secure connections between the different materials while maintaining the desired low profile. Further, it can be important to provide a smooth transition between regions of different stiffness in a guide wire to minimize the potential of kinking.

It is also desirable to provide a guide wire with a lubricious coating to facilitate advancement of the guide wire through the tortuous coronary vasculature. However, placing suitable coatings on metal guide wires raises significant manufacturing problems. Typically, the metal surface must be pretreated to allow adhesion of the lubricious coating. This adds to the expense and difficulty of producing guide wires. The present invention solves these and other problems.

SUMMARY OF THE INVENTION

This invention is directed to an elongate intraluminal device having an elongate core member with a proximal portion, an intermediate portion and a distal portion with a first polymeric jacket and a second polymeric jacket disposed about the core member. In a preferred embodiment, the first polymeric jacket is disposed about the intermediate portion of the elongate core and the second polymeric jacket is disposed about the distal portion of the core. Preferably, the intraluminal device is a guidewire and the first polymeric jacket is composed of a different polymer than the second polymeric jacket, or the first polymeric jacket has different polymeric properties than the second polymeric jacket. The use of different polymers or polymer properties imparts different handling characteristics to the various portions of the guide wire. Preferably, the first polymeric jacket is harder or has a higher shore hardness than the second polymeric jacket so that the distal portion of the guide wire is more flexible than the intermediate portion.

The polymeric jackets may comprise any suitable polymers such as polyurethanes or fluoropolymers. In one preferred embodiment, the first jacket comprises polyurethane having a shore hardness of up to about 70 D, preferably about 50 D to about 60 D. The second jacket is generally is of a softer or more flexible material than the first jacket. Typically a polyurethane having a shore hardness of about 75 A to about 100 A, preferably about 85 A to about 95 A is used for the second jacket. In a typical embodiment, a first jacket of shore hardness 55 D is used with a second jacket having a durometer of 90 A. While the use of two discrete polymer jackets is preferred, the invention is also directed to the use of three or more polymer jackets as well as a single polymer jacket having a continuously varying shore hardness over a longitudinal length of the single polymer jacket. In another preferred embodiment, the first jacket is made of polyurethane while the second jacket is made of a fluoropolymer. In embodiments where the guide wire has a shapeable coil at the distal tip, the second jacket should cover the coil.

The invention also includes a processes for making guide wires having multiple polymeric jackets or a jacket of continuously varying characteristics to impart differing handling characteristics to different portions of the guide wire. Preferably, the process involves jacketing the guide wire by hot die necking. In embodiments where the guide wire has a shapeable coil over a core member, it may be desirable to configure the process so that gaps between the turns of the coil and between the coil and the core member are filled with polymeric material to minimize any air voids.

BRIEF DESCRIPTION OF THE DRAWINGS

FIG. 1 illustrates a guide wire of the invention having a shapeable coil tip and first and second polymeric jackets.

FIGS. 2 and 3 are cross sections of the guide wire of FIG. 1 showing the first and second polymeric jackets.

FIG. 4 shows an alternate embodiment of the invention having different configuration of polymeric jackets.

FIGS. 5 and 6 are cross sections of the guide wire of FIG. 4 showing the first and second polymeric jackets.

FIG. 7 is another embodiment of the invention with first and second polymeric jackets and without a helical coil distal tip.

FIGS. 8–10 are cross sections of the guide wire of FIG. 7 showing the first, second and third polymeric jackets.

DETAILED DESCRIPTION OF THE INVENTION

Figure 11:
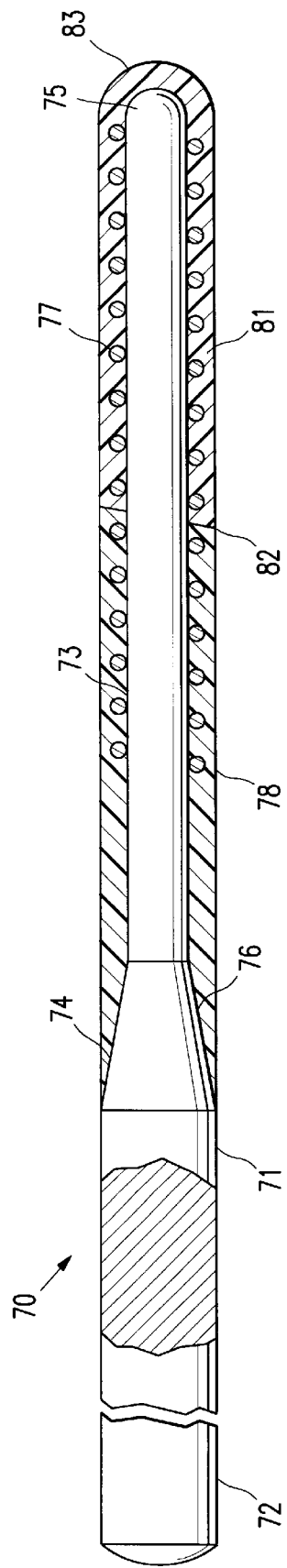
FIG. 11 is an elevational view in partial section of a guidewire having features of the invention.

As shown in FIGS. 1–3, a guide wire 10 of the present invention generally comprises a proximal core portion 12, an intermediate core portion 14 and a distal core portion 16. Running through the proximal, intermediate and distal core portions of the guide wire 10 is an elongated core member 18 typically having varying diameters to provide different handling characteristics to the different portions of the guide wire. A typical 0.014 inch diameter guide wire to be used in coronary applications will preferably have sections with diameters of about 0.014 in., 0.010 to 0.007 in., 0.005 to 0.004 in., and 0.003 to 0.002 in. extending from the proximal end to the distal end. However, other diameters are also suitable for the invention depending on the application. For example, guide wires used in the peripheral vasculature would be correspondingly larger. Generally, elongate core member 18 of guide wire 10 is stainless steel, but it may also comprise a shape memory material such as nickel-titanium alloys or other materials. Guide wire 10 has a shapeable distal tip 20 that comprises a flexible helical coil 22. The distal end has a rounded end 24, preferably formed by a solder plug securing helical coil 22 to core member 18.

As shown in the cross sections FIGS. 2 and 3, polymeric jackets 26 and 28 surround intermediate core portion 14 and distal core portion 16, respectively. In this embodiment, the polymeric jackets comprise polyurethane, with jacket 26 having a shore hardness of about 50 D to about 60 D and jacket 28 having a shore hardness of about 85 A to about 95 A. By selecting different grades of polymer, the intermediate 14 and distal 16 portions of guide wire 10 can be given different handling characteristics. In some embodiments, it may be preferable to configure the guide wire so that any spaces between the individual coils of the helical coil 22 or between the coil 22 and the core member 18 are substantially filled by polymeric jacket 28.

FIGS. 4–6 show an alternative embodiment, wherein guide wire 30 comprises proximal 32, intermediate 34 and distal 36 core portions formed from elongated core member 38. Guide wire 30 also has a shapeable distal tip 40, comprising helical coil 42 secured to core member 38. Cross sections FIGS. 5 and 6 show polymeric jackets 46 and 48 surrounding intermediate core portion 34 and distal core portion 36, respectively. In this embodiment, polymeric jacket 46 comprises polyurethane while jacket 28 comprises a fluoropolymer such as polytetrafluoroethylene (PTFE). As before, selecting different types of polymers for the two jackets imparts different mechanical and handling characteristics to the different regions of the guide wire.

FIGS. 7–10 show yet another embodiment of the invention, wherein guide wire 50 similarly comprises proximal 52, intermediate 54 and distal 56 core portions formed from elongated core member 58. However, the shapeable distal tip comprises a shapeable ribbon 60 rather than a helical coil. FIGS. 8–10 show cross sections of guide wire 50, wherein the intermediate core portion 54 has polymeric jacket 62, distal core portion 56 has polymeric jacket 64 and a third polymeric jacket 66 bridges the intermediate core portion 54 and the distal core portion 56. As before, the jackets desirably have polymers of different type or grade so that the intermediate and distal portions of the guide wire may be designed to have different handling characteristics. The use of a third type of polymer for the third jacket 66 provides greater control over the handling characteristics of the guide wire.

Further, polymeric jackets 62, 64 and 66 have a lubricious coating 68 to facilitate travel of the guide wire 50 through a patient's vasculature. A lubricious coating is very easy to apply to polymers and thus this avoids the difficulties attendant in obtaining adequate adhesion of a lubricious coating to the metal of the guide wire. In addition, while the materials for polymer jackets 62, 64, and 66 can be chosen for mechanical properties, the polymers of the jackets can also be selected for surface characteristics. The lubricious, hydrophylic, and hydrophobic characteristics of polymers used for polymer jackets 62, 64, and 66 can be selected to provide optimum performance of the guidewire 50.

While polymer jackets 62, 64 and 66 have been described as discrete, it is also possible for the jackets to be blended together at the boundaries therebetween, or for any single jacket member to have a varying composition over its entire length that varies the shore hardness of the jacket over the length. For example, in FIG. 7, if jackets 62, 64 and 66 are combined into a single jacket member, that jacket member can have a hardness of about 50 D to about 60 D, preferably about 55 D at a proximal end of the combined jacket and a hardness of about 85 A to about 95 A, preferably about 90 A at a distal end of the combined jacket. The hardness variation from the proximal end of the jacket to the distal end of the jacket could vary in any useful continuous manner including linearly or according to some other desired function. A continuous variation in shore hardness of a polymer jacket can be achieved by varying the mixture of two polymers having different shore hardnesses during the extrusion process. Another method for varying the shore hardness of a single polymer jacket is to radiation treat the polymer jacket to a varying degree along its longitudinal length. It is known in the art that certain types of gamma or e-beam radiation can alter the shore hardness of certain polymers depending on the intensity and duration of exposure.

The invention also comprises processes for manufacturing guide wires having the features described above. Generally, the process of the invention includes the steps of providing a guide wire having proximal, intermediate and distal core portions; jacketing the intermediate core portion with a first polymeric material and jacketing the distal core portion with a second polymeric material. The polymeric materials should be processed so that they conform closely to the elongated core member and the shapeable distal tip. Preferably, tubes or sleeves of polymeric material are hot die necked onto the guide wire. As an alternative, tubes or sleeves of suitable polymeric material can be heat shrunk over an elongate core member to produce the desired result. In some embodiments, it may be desirable to minimize any air gaps between the helical coil itself or between the coil and the core member. This may be achieved by heating the die to assure the polymer flows into the coil. Additionally, a lubricious coating may be applied to the surface of at last a portion of the polymeric jackets. Homopolymers, copolymers, blends, and coextrusions may be used to vary the properties of the polymers.

As discussed above the polymeric material may be any suitable, biocompatible material including polymers such as polyurethane, fluoropolymers such as polytetrafluoroethylene, PVC, polyimide, polyamide, Nylon PET, PEEK and the like. In one preferred embodiment, a guide wire is jacketed with a first polymeric material comprising polyurethane and a second polymeric material comprising polytetrafluoroethylene. Where the first and second polymeric material are the same, different grades or shore hardnesses should be used to impart different handling characteristics to the different portions of the guide wire. For example, in another preferred embodiment, a guide wire is jacketed with a first polymeric material comprising polyurethane having a hardness of about 55 D and a second polymeric material comprising polyurethane having a hardness of about 90 A. In yet other embodiments, it may be desirable to provide more than two different polymeric jackets in order to impart a greater range of handling characteristics to the guide wire. In addition to shore hardness, other characteristics of the polymeric jackets can be varied to produce the desired performance. For example, the radiopacity of the polymeric jackets could be varied by including differing percentages by weight of radiopaque materials in the polymer material. Suitable radiopaque materials would include tantalum powder, barium sulfate, bismuth, gold, platinum and the like.

FIG. 11 shows an alternative embodiment of a guidewire 70 having features of the invention. The guidewire 70 has an elongate core member 71 with a proximal core section 72 and a distal core section 73. The distal core section has a proximal end 74 and a distal end 75 which is preferably rounded. The distal core section 73 has a tapered segment 76 located at the proximal end 74. A helical coil 77 is disposed about a portion of the distal core section 73. The helical coil 77 is preferably made from a radiopaque metal such as gold, platinum, tantalum, iridium or the like, but can also be made out of stainless steel or other suitable alloys. A first polymer jacket 78 and second polymer jacket 81 are disposed about the distal core section 73 and encompass the helical coil 77 and any gaps between portions of the helical coil. The first polymer jacket 78 and second polymer jacket 81 are joined at lap joint 82. The lap joint 82 is angled with respect to a line perpendicular to a longitudinal axis of the elongate core member 71. The angled lap joint 82 provides a strong smooth transition between the first polymer jacket 78 and second polymer jacket 81. The second polymer jacket 81 has a distal end 83 that is preferably rounded to reduce trauma to the inside surface of a patient's body passageways in which the guidewire 70 is advancing.

The distal core section 73 of the elongate core member 71 has a substantially constant outer diameter over a length thereof. The outer diameter of the distal section is about 0.002 to about 0.01 inches, preferably about 0.005 to about 0.007 inches. The length of the distal core section 73 is about 10 to about 60 cm, preferably about 20 to about 40 cm. The proximal core section 72 has an outer diameter of about 0.011 to about 0.015 inches, preferably about 0.012 to about 0.014 inches. The elongate core member 71 is made of stainless steel, but could also be made of pseudoelastic alloys such as NiTi, or high strength precipitation hardenable alloys such as MP35N, L605, precipitation hardenable stainless steel or the like. The first polymer jacket 78 is made from a polyurethane with a shore hardness of about 55 D to about 65 D. The second polymer jacket 81 is made from a polyurethane with a shore hardness of about 75 A to about 85 A. As with the previously described embodiments of the invention, the first and second polymer jackets 78 and 81 can be made from a variety of polymer materials including polyamides, copolymers, and nylons such as Pebax. Although guidewire 70 is shown in FIG. 11 with two polymer jackets, three or more polymer jackets could be used to cover or partially cover the distal core section 73 of the elongate core member. Also, in addition to multiple polymer jackets that are softer and more flexible distally along the elongate core member 71, alternative configurations could be used whereby an intermediate polymer jacket has a shore hardness less than a proximal polymer jacket located proximally to the intermediate polymer jacket and less than a distal polymer jacket located distal to the intermediate polymer jacket. This would give the guidewire a distal section with a more flexible intermediate portion.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire comprising an elongate core member having a proximal portion, an intermediate portion and a distal portion having a most distal end, a first polymeric jacket disposed about at least part of the intermediate portion and a second polymeric jacket formed at least in part of a fluoropolymer disposed about at least part of the most distal end of the distal portion.

2. The guide wire of claim 1 wherein the first and second polymeric jackets have different physical characteristics.

3. The guide wire of claim 2 wherein the first and second polymeric jackets have different shore hardnesses.

4. The guide wire of claim 2 further comprising at least one additional polymeric jacket disposed about the elongate core member and having physical characteristics different from the first and second polymeric jacket.

5. The guide wire of claim 3 wherein the first polymeric jacket comprises polyurethane having a shore hardness of about 50 D to about 60 D, and the second polymeric jacket comprises polyurethane having a shore hardness of about 85 A to about 95 A.

6. The guide wire of claim 3 wherein the first polymeric jacket comprises a polyurethane and the second polymeric jacket comprises a fluoropolymer.

7. The guide wire of claim 1 wherein a distal portion of the guide wire further comprises a shapeable coil secured to the elongate core member and wherein the second polymeric jacket is disposed about the shapeable coil.

8. The guide wire of claim 7 wherein shapeable coil has spaces between adjacent coils and spaces between the shapeable coil and the elongate core member and wherein the polymeric jacket fills substantially all the spaces.

9. A guidewire comprising an elongate core member having a proximal portion, an intermediate portion and a distal portion having a most distal end, and a polymeric jacket disposed about at least part of the intermediate portion and at least part of the most distal end of the distal portion and having a shore hardness that varies continuously along the longitudinal length of the polymer jacket.

10. The guide wire of claim 9 wherein the polymer jacket further comprises a proximal end and a distal end and varies linearly in shore hardness from about 55 D at a proximal end to about 90 A at a distal end.

* * * * *